United States Patent

Nadelson

Patent Number: 4,681,898
Date of Patent: Jul. 21, 1987

[54] N-N-DISUBSTITUTED ALKENAMIDES AND PHENYLALKENAMIDES

[75] Inventor: Jeffrey Nadelson, Denville, N.J.

[73] Assignee: Sandoz Pharmaceuticals Corp., E. Hanover, N.J.

[21] Appl. No.: 608,126

[22] Filed: May 8, 1984

Related U.S. Application Data

[63] Continuation-in-part of Ser. No. 505,804, Jun. 20, 1983, abandoned, which is a continuation-in-part of Ser. No. 330,601, Dec. 14, 1981, abandoned.

[51] Int. Cl.$^4$ .................................. C07C 103/22
[52] U.S. Cl. ........................ 514/619; 514/620; 514/621; 514/866; 564/163; 564/164; 564/165; 564/169; 564/193; 564/196; 564/199; 564/200
[58] Field of Search ............ 564/163, 164, 165, 169, 564/193, 196, 199, 200; 514/619, 620, 621, 866

[56] References Cited

U.S. PATENT DOCUMENTS

| | | | |
|---|---|---|---|
| 4,039,589 | 8/1977 | Toth et al. | 564/354 X |
| 4,061,776 | 12/1977 | Kikumoto et al. | 564/353 X |
| 4,605,672 | 8/1986 | Toth et al. | 564/324 X |

Primary Examiner—Robert V. Hines
Attorney, Agent, or Firm—Gerald D. Sharkin; Robert S. Honor; Thomas O. McGovern

[57] ABSTRACT

Compounds of the formula

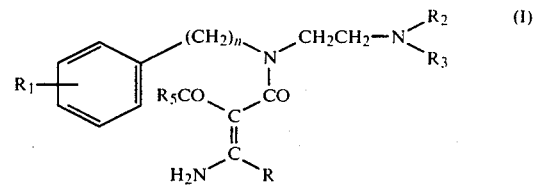

where
n is 0 or 1,
R is alkyl, phenyl or $R_4$-substituted phenyl,
$R_2$ and $R_3$ are, independently, alkyl or
$R_2$ and $R_3$ together with N is

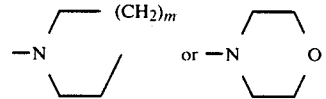

m is 1, 2 or 3,
$R_1$ and $R_4$ are, independently hydrogen, halo, alkyl or alkoxy, and
$R_5$ is hydrogen or alkyl of 1 to 6 carbon atoms
or their pharmaceutically acceptable salts are useful as anti-diabetic agents, in particular, as hypoglycemic agents or inhibitors of post-prandial hypoglycemia.

13 Claims, No Drawings

N-N-DISUBSTITUTED ALKENAMIDES AND PHENYLALKENAMIDES

This is a continuation in part of U.S. patent application Ser. No. 505,804, filed June 20, 1983, and now abandoned which in turn is a continuation in part of U.S. patent application Ser. No. 330,601, filed Dec. 14, 1981 and now abandoned.

This invention relates to N,N-disubstituted alkenamides and phenylalkenamides, which exhibit anti-diabetic activity. In particular, it relates to N-phenyl or phenalkyl-N-substituted aminoethyl-2-acetyl-3-amino-alkenamides and phenalkenamides and their pharmaceutically acceptable salts and to processes and intermediates for their preparation.

The compounds of this invention may be represented by the following structural formula:

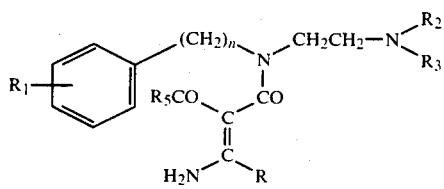

where
n is 0 or 1
R is lower alkyl, i.e., straight or branch chain alkyl having 1 to 4 carbon atoms, e.g., methyl, ethyl, isopropyl and the like, or

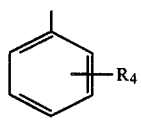

$R_2$ and $R_3$ are each, independently, lower alkyl as defined above, or
$R_2$ and $R_3$ together with the nitrogen to which they are attached is

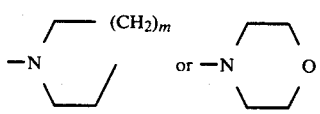

where m is 1, 2 or 3;
$R_1$ and $R_4$ are each, independently, hydrogen, halo having an atomic number of about 19 to 36, lower alkyl as defined above or lower alkoxy, i.e., alkoxy having 1 to 4 carbon atoms, e.g., methoxy, ethoxy, and the like; and
$R_5$ is hydrogen or alkyl of 1 to 6 carbon atoms; or a pharmaceutical acceptable salt thereof.
Halo is fluoro or chloro, preferably fluoro and n is preferably O.

The compounds of formula (I) may exist in the following tautomeric forms:

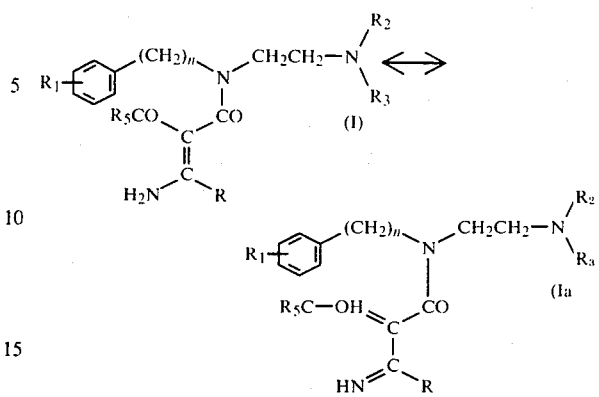

The compounds of formula (I) can also exist in the following geometrical form:

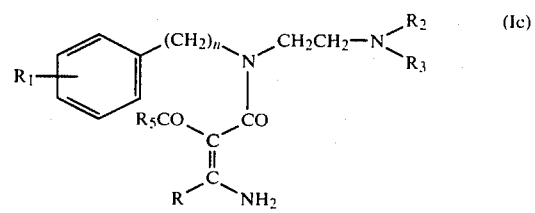

All of the tautomeric forms and geometrical isomers and their pharmaceutically acceptable salts are included within the scope of the presently claimed invention.

The compound of formula (I) may be prepared in accordance with the following reaction scheme:

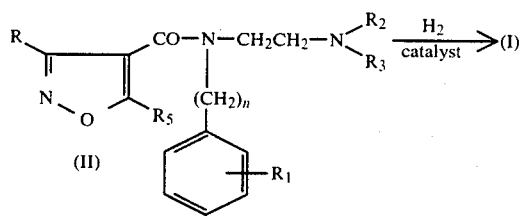

where n, R, $R_1$, $R_2$, $R_3$ and $R_5$ are as defined above.

The compounds of formula (I) are prepared by reducing a compound of the formula (II) in an inert organic solvent under hydrogen in the presence of a hydrogenation catalyst. The particular catalyst used is not critical and can be palladium on carbon, platinum oxide, Raney nickel and the like, preferably 10% palladium on carbon. The hydrogenation is carried out at pressures of from 14 psi to 100 psi, preferably 35 to 70 psi. Although the particular solvent used is also not critical, it is preferred that the reaction be carried out in solvents such as the lower alkanols, e.g., methanol, ethanol and the like or dimethylformamide. Alkanols are preferred when the reaction is carried out at room temperature; and dimethylformamide is preferred at the higher temperatures. The temperature at which the reaction is run is not critical, but it is preferred that the reaction be carried out between about 20° C. to 100° C., especially between about 20° C. to 70° C. The time of the reaction also is not critical, although it is preferred that the reaction be run for 5 hours to 24 hours, especially 16 hours to 20 hours. The compound of formula (I) is isolated by conventional techniques, e.g., evaporation and recrystallization.

The compound of formula (II) may be prepared in accordance with the following reaction scheme:

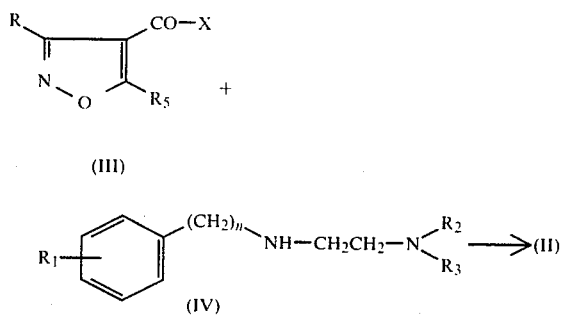

where
X is chloro or bromo, and
n, R, $R_1$, $R_2$ and $R_3$ are as defined above.

The compounds of formula (II) are prepared by reacting a compound of the formula (III) with a compound of formula (IV) in an inert solvent, preferably in the presence of an acid scavenger such as triethylamine, diisopropylethylamine, pyridine, or potassium or sodium bicarbonate. Triethylamine is the preferred reagent. Although the particular solvent used is not critical, it is preferred that the reaction be carried out in an inert solvent such as ethers, e.g., tetrahydrofuran or diethyl ether; aromatic hydrocarbons such as benzene or toluene or chlorinated hydrocarbons, e.g., methylene dichloride or chloroform, especially tetrahydrofuran. The temperature at which the reaction is run is not critical, but it is preferred that the reaction be carried out between about $-30°$ C. to $100°$ C., preferably between about $20°$ C. to $30°$ C. The time of the reaction also is not critical, although it is preferred that the reaction be run for 1 to 18 hours, especially 3 to 7 hours. The compound of formula (II) is isolated by conventional techniques, e.g., evaporation and recrystallization.

The compounds of formula II especially the compounds in which $R_1$ is fluoro, may also be prepared in accordance with the following reaction scheme:

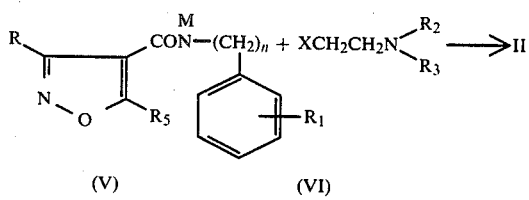

where
M is an alkali cation,
X is chloro or bromo and
n, R, $R_1$, $R_2$, $R_3$ and $R_5$ are as defined above.

The compounds of formula (II) are prepared by treating a compound of the formula (V) with a compound of the formula (VI) in the presence of an inert organic solvent. Although the particular solvent employed is not critical, the preferred solvents include dimethylformamide, dimethylsulfoxide, ethers such as diethylether or tetrahydrofuran, or aromatic hydrocarbons such as benzene, toluene, xylene and the like, preferably dimethylformamide. The temperature of the reaction is not critical, but it is preferred that the reaction be run at a temperature of from about $25°$ to $100°$ C., preferably from about $50°$ to $90°$ C. The reaction is run from about 10 to 48 hours, preferably from about 15 to 36 hours.

The product is recovered using conventional techniques, e.g., evaporation.

The compound of formula (V) may be prepared in accordance with the following reaction scheme:

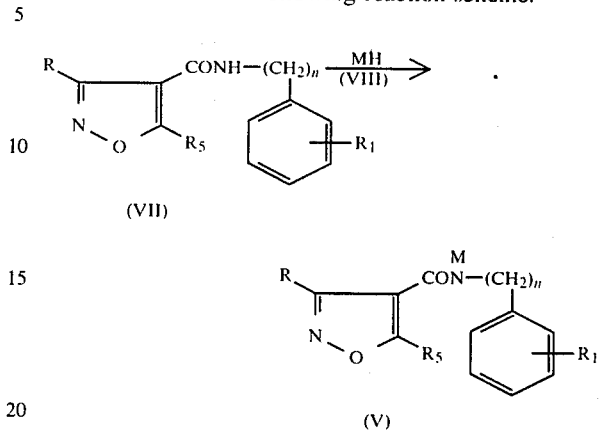

where
MH is an alkali metal hydride, and
n, R, $R_1$ and $R_5$ are as defined above.

The compounds of formula (V) are prepared by treating a compound of the formula (VII) with an alkali metal hydride of the formula (VIII) in the presence of an inert organic solvent. The alkali metal hydride can be sodium hydride, potassium hydride, and the like, preferably sodium hydride. Although the particular solvent employed is not critical, the preferred solvents include dimethylformamide, dimethylsulfoxide, ethers, such as diethylether or tetrahydrofuran or aromatic hydrocarbons, such as benzene, toluene and the like, preferably dimethylformamide. The temperature of the reaction is not critical, but it is preferred that the reaction be run at a temperature of from about $0°$ to $50°$ C., preferably from about $20°$ to $30°$ C. The reaction is run from about 1 to 10 hours, preferably from about 2 to 7 hours. The product of the compound of formula (V) is not isolated but is employed in situ as a starting material in the preparation of the compounds of formula (II).

The compounds of formula (VII) may be prepared in accordance with the following reaction scheme:

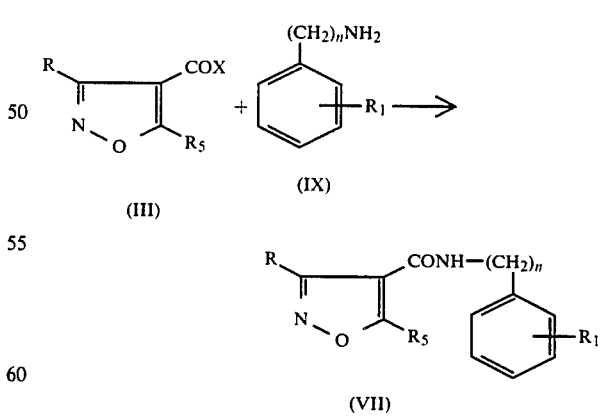

where n, R, $R_1$, $R_5$ and X are as defined above.

The compounds of formula (VII) are prepared by reacting a compound of the formula (III) with a compound of formula (IX) under essentially the same condition used in preparing the compounds of formula (II) above. The preferred solvent is toluene and the reaction is preferably carried out at 20° to 35° C. for 1 to 18 hours.

Many of the compounds of formula III, IV, VI, VIII, and IX are known and can be prepared by methods described in the literature. The compounds of formula III, IV, VI, VIII and IX not specifically disclosed in the literature may be prepared by analogous methods using known starting materials.

The compounds of formula (I), and their pharmaceutically acceptable salts, are useful because they exhibit pharmacological activity in animals. In particular, the compounds of formula (I) are useful in the treatment of diabetes as hypoglycemic agents and by inhibiting or impeding post-prandial hyperglycemia.

The compounds of formula (I) are useful in the treatment of diabetes as hypoglycemic agents as indicated by the lowering of blood glucose in male Wistar rats weighing 200±10 grams. The test animals are fasted in groups of 5–7 for 16 hours and then are dosed with 50 to 100 milligrams per kilogram of animal body weight of the compound orally. The animals are maintained on water; and two hours after the test compound is administered, the rats are anesthetized with ether and blood is collected via cardiac puncture. The serum glucose level is determined by the Technicon Auto-Analyzer II (glucose oxidase method). These glucose levels are then compared with the glucose level of a control group, which receives orally 0.5% carboxymethyl cellulose and is run concurrently.

The compounds of formula (I) are also useful in the treatment of diabetes by inhibiting or impeding post-prandial hyperglycemia as indicated by a lowering of the serum glucose levels in male Wistar rats weighing 200±10 grams after an oral starch load. In this test, male Wistar rats is groups of 5–7 are fasted for 16 hours and then are dosed with 50 to 200 mg/kg p.o. of the test compound. One hour later, the rats are given orally 1.0 gram per kilogram of animal body weight of a cooked starch load. Thirty minutes after administration of the starch, the rats are anesthetized with 120 milligrams per kilogram of animal body weight of sodium hexobarbital after which blood is collected via cardiac puncture. The serum is used to determine the sugar level with a Technicon Auto-Analyzer II (glucose oxidase method). The serum glucose content is compared to the control group which receives 0.5% carboxymethyl cellulose and an oral starch load and are run concurrently.

The use of the compounds of formula (I) in the treatment of diabetes by inhibiting post-prandial hyperglycemia is also indicated by the lowering of serum glucose in 4 male cebus monkeys weighing 2 to 4 kilograms which are fasted for 16 to 18 hours before testing. At least a three-day interval is allowed between experimental days. The compound to be tested is suspended in 0.5% carboxymethyl cellulose (CMC) for oral dosing. Two blood samples for basal serum glucose level are taken at minus 30 min. and just before administration of placebo (0.5% CMC) or the test compound at 5, 10, 20 and 40 mg/kg of animal body weight. One hour later the animals are given, orally 1.5 gram per kilogram of weight of a cooked starch load. Blood samples are thereafter taken hourly for 4 hours. Serum glucose levels were determined by the Technicon Auto-Analyzer II (glucose oxidase method), and these glucose levels are then compared with the glucose levels of the control group which received orally 0.5% CMC and is run concurrently.

For the inhibition of post-prandial hyperglycemia and use as a hypoglycemic agent, the compounds of formula (I) and their non-toxic, pharmaceutically acceptable salts may be administered orally or parenterally as such or admixed with conventional pharmaceutical carriers. They may be administered orally in such forms as tablets, dispersible powders, granules, capsules, syrups and elixirs, and parenterally as solutions, e.g., a sterile injectable aqueous solution. The composition for oral use may contain one or more conventional adjuvants, such as sweetening agents, flavoring agents, coloring agents and preserving agents, in order to provide an elegant and palatable preparation. Tablets may contain the active ingredient in admixture with conventional pharmaceutically acceptable excipients, e.g., inert diluents, such as calcium carbonate, sodium carbonate, lactose, and talc, granulating and disintegrating agents. e.g., starch and alginic acid, binding agents, e.g., magnesium stearate, stearic acid and talc. The tablets may be coated by known techniques to delay disintegration and absorption in the gastro-intestinal tract and thereby provide a sustained action over a longer period. Similarly, suspensions, syrups and elixirs may contain the active ingredient in admixture with any of the conventional excipients utilized in the preparation of such compositions, e.g., suspending agents such as methylcellulose, tragacanth and sodium alginate; wetting agents such as lecithin, polyoxyethylene stearate and polyoxyethylene sorbitan monooleate; and preservatives such as ethyl p-hydroxybenzoate. Capsules may contain the active ingredient alone or admixed with an inert solid diluent, e.g., calcium carbonate, calcium phosphate and kaolin. The injectable compositions are formulated as known in the art. These pharmaceutical preparations may contain up to about 90% of the active ingredient in combination with the carrier or adjuvant.

The hypoglycemic effective amount of active ingredient employed in the treatment of diabetes may vary depending on the particular compound employed, the mode of administration and the severity of the condition being treated. However, in general, satisfactory results in the treatment of diabetes are obtained when a compound of formula (I), or a pharmaceutically acceptable salt thereof, is administered as a hypoglycemic agent at a daily dosage of from about 2 milligrams to about 200 milligrams, preferably 2 to 100 milligrams per kilogram of animal body weight, preferably given orally and in divided doses two or four times a day, or in sustained release form. For larger mammals, the total daily dosage is from about 100 milligrams to about 3000 milligrams, preferably 100 to 2000 milligrams. Unit dosage forms suitable for internal use comprise from about 25 milligrams to about 2000 milligrams, preferably 25 to 1500 milligrams and more preferably 25 to 1000 milligrams of the active compound in intimate admixture with a solid or liquid, pharmaceutically acceptable carrier.

The effective amount of active ingredient for inhibiting post-prandial hyperglycemia employed in the treatment of diabetes may also vary depending on the particular compound employed, the mode of administration and the severity of the condition being treated. However, in general satisfactory results in the treatment of diabetes are obtained when a compound of formula (I), or a pharmaceutically acceptable salt thereof, is administered at a daily dosage of from about 1.5 to 200 milligrams, preferably 1.5 to about 100 milligrams and especially 2 to 100 milligrams per kilogram of animal body weight, preferably given orally and in divided doses two or four times a day, or in sustained release form. For larger mammals, the total daily dosage is from about 100 milligrams to about 3000 milligrams, preferably 100 to 2000 milligrams, also preferably given at mealtime as conventional in treatments with substances having such activity, e.g., three times a day, in divided dosages of from about 40 to 1000 milligrams, preferably 40 to 700 milligrams, particularly before a carbohydrate-rich meal.

The compounds of formula (I) may be similarly administered in the form of their non-toxic pharmaceutically acceptable acid addition salts. Such salts possess the same order of activity as the free base and are readily prepared by reacting the compound with a pharmaceutically acceptable acid by conventional techniques, and, accordingly, are included within the scope of this invention. Representative of the inorganic salts are the hydrochloride, hydrobromide, hydroiodide, phosphate (including hydrogen phosphate), metaphosphate, and sulfate (including hydrogen sulfate). Representative examples of the organic salts are the acetate, maleate, fumarate and the like.

Tablets and capsules containing the ingredients indicated below may be prepared by conventional techniques and are useful in treating diabetes, at a dose or one tablet or capsule 2 to 4 times a day.

| Ingredients | Weight (mg.) tablet | capsule |
|---|---|---|
| 2-(aminophenylmethylene)-N—(2-dimethyl-aminoethyl)-N—phenyl-3-oxo-butanamide | 350 | 350 |
| tragacanth | 10 | — |
| lactose | 197.5 | 150 |
| corn starch | 25 | — |
| talcum | 15 | — |
| magnesium stearate | 2.5 | — |
| Total | 600 | 600 |

The active ingredient, 2-(aminophenylmethylene)-N-(2-dimethylaminoethyl)-N-phenyl-3-oxo-butanamide, indicated above has, for example, been determined to have an ED25 in the above hypoglycemia test of 74 mg/kg p.o. For the known compound tolbutamide, the ED25 in this test was found to be 110 mg/kg p.o. Thus, an indicated daily dosage for the active agent above would be from about 3 to about 100 mg/kg, preferably 3 to 20 mg/kg, for use as a hypoglycemic agent in treating diabetes. In the post-prandial test in the rat, the compound has been determined to have an ED50 of 25 mg/kg p.o. An indicated daily dosage for this compound in the treatment of diabetes by inhibiting post-prandial hypoglycemia would be from about 100 to 1050 milligrams.

The daily dosages suitable for any particular compound will of course depend on a number of factors including relative potency and activity. The title compound of example 3, 2-acetyl-3-amino-N-(2-dimethylaminoethyl)-N-(m-fluorophenyl)-2-pentenamide has, for example, been determined to have and ED50 of 35 mg/kg p.o. in the monkey and 50 mg/kg p.o. in the Wistar rats in the post-prandial hypoglycemia tests. An indicated daily dosage for this compound in the treatment of diabetes by inhibiting post-prandial hypoglycemia would be from about 100 to 2000 milligrams, preferably 250 to 1000 milligrams.

EXAMPLE I 2-(Aminophenylmethylene)-N-(2-Dimethylaminoethyl)-N-Phenyl)-3-oxo-Butanamide

Step 1.

N-Phenyl-N-(2-Dimethylaminoethyl)-5-Methyl-3-Phenyl-4-Isoxazole Carboxamide

A mixture of 24.6 grams (0.15 mole) of N,N-dimethyl-N'-phenyl-ethylenediamine and 18.2 grams (0.18 mole) of triethylamine in 500 milliliters of tetrahydrofuran (THF) is cooled to 0° C. and 39.8 grams (0.18 mole) of 5-methyl-3-phenyl-4-isoxazole carbonyl chloride in 100 milliliters of tetrahydrofuran is added dropwise. After the addition is complete, the mixture is warmed to room temperature and stirred for 4 hours. The resulting suspension is filtered and the THF removed in vacuo. The residue is dissolved in methylene chloride and washed with 2N sodium hydroxide and water and then dried over magnesium sulfate. The mixture is filtered and the solvent removed by evaporation. The residue is then treated with hexane to yield crystals of N-phenyl-N-(2-dimethylaminoethyl)-5-methyl-3-phenyl-4-isoxazole carboxamide; M.P. 88°–89° C.

When the N,N-dimethyl-N'-phenyl-ethylene-diamine in the above reaction is replaced by an equivalent amount of (a) N,N-dimethyl-N'-p-fluorophenyl-ethylenediamine;
(b) N,N-dimethyl-N'-p-tolyl-ethylenediamine;
(c) N,N-dimethyl-N'-p-methoxyphenyl-ethylenediamine;
(d) 2-morpholino-N-phenyl-ethylamine;
(e) 2-piperidino-N-phenyl-ethylamine;
(f) N,N-dimethyl-N'-benzyl-ethylenediamine;
(g) N,N-diethyl-N'-phenyl-ethylenediamine;
(h) N,N-diethyl-N'-m-fluorophenyl-ethylenediamine;
(i) N,N-dimethyl-N'-m-fluorophenyl-ethylenediamine; or
(j) N-(2-pyrolidinoethyl)-N-phenyl-ethylenediamine, respectively, there is obtained (a) N-(p-fluorophenyl)-N-(2-dimethylaminoethyl)-5-methyl-3-phenyl-4-isoxazole carboxamide;
(b) N-(p-tolyl)-N-(2-dimethylaminoethyl)-5-methyl-3-phenyl-4-isoxazole carboxamide;
(c) N-(p-methoxyphenyl)-N-(2-dimethylaminoethyl)-5-methyl-3-phenyl-4-isoxazole carboxamide;
(d) N-phenyl-N-(2-morpholinoethyl)-5-methyl-3-phenyl-4-isoxazole carboxamide;
(e) N-phenyl-N-(2-piperidinoethyl)-5-methyl-3-phenyl-4-isoxazole carboxamide;
(f) N-benzyl-N-(2-dimethylaminoethyl)-5-methyl-3-phenyl-4-isoxazole carboxamide (m.p. 85°–87° C.);
(g) N-phenyl-N-(2-diethylaminoethyl)-5-methyl-3-phenyl-4-isoxazole carboxamide;
(h) N-(m-fluorophenyl)-N-(2-diethylaminoethyl)-5-methyl-3-phenyl-4-isoxazole carboxamide;
(i) N-(m-fluorophenyl)-N-(2-dimethylaminoethyl)-5-methyl-3-phenyl-4-isoxazole carboxamide; or
(j) N-phenyl-N-(2-pyrolidinoethyl)-5-methyl-3-phenyl-4-isoxazole carboxamide,
respectively.

Step 2.

2-(Aminophenylmethylene)-N-(2-Dimethylaminoethyl)-N-Phenyl-3-Oxo-Butanamide

A mixture of 35 grams (0.1 mole) of N-phenyl-N-(2-dimethylaminoethyl)-5-methyl-3-phenyl-4-isoxazole carboxamide and 3.8 grams of 10% palladium on carbon in 200 milliliters of dimethylformamide is hydrogenated at 50 psi and 50°–60° C. overnight. The mixture is cooled, filtered, and the filtrate evaporated in vacuo. The residue obtained is then treated with hexane and the resulting crystals triturated with ether to give 2-(aminophenylmethylene)-N-(2-dimethylaminoethyl)-N-phenyl-3-oxobutanamide; M.P. 81°–83° C.

Following the above procedure, but using in place of the N-phenyl-N-(2-dimethylaminoethyl)-5-methyl-3-phenyl-4-isoxazole carboxamide an equivalent amount of (a) N-(p-fluorophenyl)-N-(2-dimethylaminoethyl)-5-methyl-3-phenyl-4-isoxazole carboxamide;

(b) N-(p-tolyl)-N-(2-dimethylaminoethyl)-5-methyl-3-phenyl-4-isoxazole carboxamide;

(c) N-(p-methoxyphenyl)-N-(2-dimethylaminoethyl)-5-methyl-3-phenyl-4-isoxazole carboxamide;

(d) N-phenyl-N-(2-morpholinoethyl)-5-methyl-3-phenyl-4-isoxazole carboxamide;

(e) N-phenyl-N-(2-piperidinoethyl)-5-methyl-3-phenyl-4-isoxazole carboxamide;

(f) N-benzyl-N-(2-dimethylaminoethyl)-5-methyl-3-phenyl-4-isoxazole carboxamide;

(g) N-phenyl-N-(2-diethylaminoethyl)-5-methyl-3-phenyl-4-isoxazole carboxamide, (h) N-(m-fluorophenyl)-N-(2-diethylaminoethyl)-5-methyl-3-phenyl-4-isoxazole carboxamide;

(i) N-(m-fluorophenyl)-N-(2-dimethylaminoethyl)-5-methyl-3-phenyl-4-isoxazole carboxamide; or (j) N-phenyl-N-(2-pyrolidinoethyl)-5-methyl-3-phenyl-4-isoxazole carboxamide, respectively, there is obtained (a) 2-(aminophenylmethylene)-N-(2-dimethylaminoethyl)-N-(p-fluorophenyl)-3-oxo-butanamide (m.p. 99°–100° C.);

(b) 2-(aminophenylmethylene)-N-(2-dimethylaminoethyl)-N-(p-tolyl)-3-oxo-butanamide (m.p. 107°–108° C.);

(c) 2-(amiophenylmethylene)-N-(2-dimethylaminoethyl)-N-(p-methoxyphenyl)-3-oxo-butanamide (m.p. 110°–111° C.);

(d) 2-(aminophenylmethylene)-N-(2-morpholinoethyl)-N-phenyl-3-oxo-butanamide (m.p. 138°–139° C.);

(e) 2-(aminophenylmethylene)-N-(2-piperidinoethyl)-N-phenyl-3-oxo-butanamide (m.p. 64°–65° C.);

(f) 2-(aminophenylmethylene)-N-(2-dimethylaminoethyl)-N-benzyl-3-oxo-butanamide (m.p. 105°–107° C.);

(g) 2-(aminophenylmethylene)-N-(2-diethylaminoethyl)-N-phenyl-3-oxo-butanamide (m.p. 62°–63° C.);

(h) 2-(aminophenylmethylene)-N-(2-diethylaminoethyl)-N-(m-fluorophenyl-3oxo-butanamide (m.p. 84°–85° C.);

(i) 2-(aminophenylmethylene)-N-(2-dimethylaminoethyl)-N-(m-fluorophenyl)-3-oxo-butanamide (m.p. 128.5°–129.5° C. as the maleate salt); or (j) 2-(aminophenylmethylene)-N-(2-pyrolidinoethyl)-N-phenyl-3-oxo-butanamide (m.p. 169°–171° C.) as the maleate salt), respectively.

EXAMPLE 2

2-Acetyl-3-Amino-N-(2-Dimethylaminoethyl)-N-Phenyl-2-Pentenamide

Step 1.

N-Phenyl-N-(2-dimethylaminoethyl)-3-Ethyl-5-Methyl-4-Isoxazole Carboxamide

A mixture of 24.6 grams (0.15 mole) of N,N-dimethyl-N'-phenyl-ethylenediamine and 18.2 grams (0.18 mole) of triethylamine in 500 milliliters of tetrahydrofuran is cooled to 0° and 30.8 grams (0.18 mole) of 3-ethyl-5-methyl-4-isoxazole carbonyl chloride in 100 milliliters of tetrahydrofuran is added dropwise. After the addition is complete, the mixture is warmed to room temperature and stirred for 4 hours. The resulting suspension is filtered and the THF removed in vacuo. The residue is dissolved in methylene chloride, washed with 2N sodium hydroxide and water and then dried over magnesium sulfate. The mixture is filtered and the solvent removed by evaporation. The residue is dissolved in ethanol and treated with maleic acid to give N-phenyl-N-(2-dimethylaminoethyl)-3-ethyl-5-methyl-4-isoxazole-carboxamide maleate; m.p. 140°–142° C.

When the above reaction is carried out using in place of the N,N-dimethyl-N'-phenyl-ethylenediamine, an equivalent amount of (k) N,N-dimethyl-N'-benzyl-ethylenediamine;

(l) N,N-dimethyl-N'-(o-fluorophenyl)-ethylenediamine;

(m) N,N-dimethyl-N'-(m-fluorophenyl)-ethylenediamine (n) N,N-dimethyl-N'-(p-fluorophenyl)-ethylenediamine, (o) N,N-diisopropyl-N'-phenyl-ethylenediamine;

(p) N,N-dimethyl-N'-o-tolyl-ethylenediamine;

(q) N,N-dimethyl-N'-o-methoxyphenyl-ethylenediamine; or (r) N,N-diethyl-N'-o-fluorophenyl-ethylenediamine, there is obtained (k) N-benzyl-N-(2-dimethylaminoethyl)-3-ethyl-5-methyl-4-isoxazole carboxamide (m.p. 69°–71° C. as citrate);

(l) N-(o-fluorophenyl)-N-(2-dimethylaminoethyl)-3-ethyl-5-methyl-4-isoxazole carboxamide (oil);

(m) N-(m-fluorophenyl)-N-(2-dimethylaminoethyl)-3-ethyl-5-methyl-4-isoxazole carboxamide (m.p. 162°–164° C. as HCl);

(n) N-(p-fluorophenyl)-N-(2-dimethylaminoethyl)-3-ethyl-5-methyl-4-isoxazole carboxamide (oil);

(o) N-phenyl-N-(2-diisopropylaminoethyl)-3-ethyl-5-methyl-4-isoxazole carboxamide;

(p) N-(m-tolyl)-N-(2-dimethylaminoethyl)-3-ethyl-5-methyl-4-isoxazole carboxamide;

(q) N-(o-methoxyphenyl)-N-(2-dimethylaminoethyl)-3-ethyl-5-methyl-4-isoxazole carboxamide, or (r) N-(o-fluorophenyl)-N-(2-diethylaminoethyl)-3-ethyl-5-methyl-4-isoxazole carboxamide, respectively.

When the above reaction is carried out using in place of the 3-ethyl-5-methyl-4-isoxazole carbonyl chloride, an equivalent amount of (s) 3-ethyl-4-isoxazole carbonyl chloride;

(t) 3,5-diethyl-4-isoxazole carbonyl chloride;

(u) 3-ethyl-5-propyl-4-isoxazole carbonyl chloride;

(v) 3,5-dimethyl-4-isoxazole carbonyl chloride, or (w) 3-methyl-5-isopropyl-4-isoxazole-carbonyl chloride, there is obtained (s) N-phenyl-N-(2-dimethylaminoethyl)-3-ethyl-4-isoxazole carboxamide (oil);
(t) N-phenyl-N-(2-dimethylaminoethyl)-3,5-diethyl-4-isoxazole carboxamide (oil);
(u) N-phenyl-N-(2-dimethylaminoethyl)-3-ethyl-5-propyl-4-isoxazole carboxamide;
(v) N-phenyl-N-(2-dimethylaminoethyl)-3,5-dimethyl-4-isoxazole carboxamide; or
(w) N-phenyl-N-(2-dimethylaminoethyl)-3-methyl-5-isopropyl-4-isoxazole carboxamide,
respectively.

Step 2.
2-Acetyl-3-Amino-N-(2-Dimethylaminoethyl)-N-Phenyl-2-Pentenamide A mixture of 51.2 grams (0.17 mole) of N-phenyl-N-(2-dimethylaminoethyl)-3-ethyl-5-methyl-4-isoxazole carboxamide and 5.2 grams of 10% palladium on carbon in 200 milliliters ethanol is hydrogenated at 50 pounds per square inch at room temperature overnight. The catalyst is removed by filtration and the solvent is evaporated in vacuo. The residue obtained is then treated with hexane and the resulting crystals triturated with ether to give 2-acetyl-3-amino-N-(2-dimethylaminoethyl)-N-phenyl-2-pentenamide, m.p. 103°–105° C.

Following the above procedure, but using in place of the N-phenyl-N-(2-dimethylaminoethyl)-3-ethyl-5-methyl-4-isoxazole carboxamide, an equivalent amount of (k) N-benzyl-N-(2-dimethylaminoethyl)-3-ethyl-5-methyl-4-isoxazole carboxamide;
(l) N-(o-fluorophenyl)-N-(2-dimethylaminoethyl)-3-ethyl-5-methyl-4-isoxazole carboxamide;
(m) N-(m-fluorophenyl)-N-(2-dimethylaminoethyl)-3-ethyl-5-methyl-4-isoxazole carboxamide;
(n) N-(p-fluorophenyl)-N-(2-dimethylaminoethyl)-3-ethyl-5-methyl-4-isoxazole carboxamide;
(o) N-phenyl-N-(2-diisopropylaminoethyl)-3-ethyl-5-methyl-4-isoxazole carboxamide;
(p) N-(o-tolyl)-N-(2-dimethylaminoethyl)-3-ethyl-5-methyl-4-isoxazole carboxamide;
(q) N-(o-methoxyphenyl)-N-(2-dimethylaminoethyl)-3-ethyl-5-methyl-4-isoxazole carboxamide;
(r) N-(o-fluorophenyl)-N-(2-diethylaminoethyl)-3-ethyl-5-methyl-4-isoxazole carboxamide;
(s) N-phenyl-N-(2-dimethylaminoethyl)-3-ethyl-4-isoxazole carboxamide;
(t) N-phenyl-N-(2-dimethylaminoethyl)-3,5-diethyl-4-isoxazole carboxamide;
(u) N-phenyl-N-(2-dimethylaminoethyl)-3-ethyl-5-propyl-4-isoxazole carboxamide;
(v) N-phenyl-N-(2-dimethylaminoethyl)-3,5-dimethyl-4-isoxazole carboxamide; or
(w) N-phenyl-N-(2-dimethylaminoethyl)-3-methyl-5-isopropyl-4-isoxazole carboxamide,
there is obtained
(k) 2-acetyl-3-amino-N-2-(dimethylaminoethyl)-N-benzyl-2-pentenamide (m.p. 123°–125° C.);
(l) 2-acetyl-3-amino-N-(2-dimethylaminoethyl)-N-(o-fluorophenyl)-2-pentenamide (m.p. 98.5°–100° C.);
(m) 2-acetyl-3-amino-N-(2-dimethylaminoethyl)-N-(m-fluorophenyl)-2-pentenamide (m.p. 96°–97° C.);
(n) 2-acetyl-3-amino-N-(2-dimethylaminoethyl)-N-(p-fluorophenyl)-2-pentenamide (m.p. 89°–91° C.);
(o) 2-acetyl-3-amino-N-(2-diisopropylaminoethyl)-N-phenyl-2-pentenamide (m.p. 114°–115° C.);
(p) 2-acetyl-3-amino-N-(2-dimethylaminoethyl)-N-(o-tolyl)-2-pentenamide (m.p. 98°–99° C.);
(q) 2-acetyl-3-amino-N-(2-dimethylaminoethyl)-N-(o-methoxyphenyl)-2-pentenamide (m.p. 114.5°–116.5° C.);
(r) 2-acetyl-3-amino-N-(2-diethylaminoethyl)-N-(o-fluorophenyl)-2-pentenamide (m.p. 69°–71° C.);
(s) 2-formyl-3-amino-N-(2-dimethylaminoethyl)-N-phenyl-2-pentenamide (m.p. 163°–165.5° C. as the oxalate salt);
(t) 2-propionyl-3-amino-N-(2-dimethylaminoethyl)-N-phenyl-2-pentenamide (m.p. 140°–141° C. as the oxalate salt);
(u) 2-butyryl-3-amino-N-(2-dimethylaminoethyl)-N-phenyl-2-pentenamide (m.p. 164°–165° C. as the oxalate salt);
(v) 2-acetyl-3-amino-N-(2-dimethylaminoethyl)-N-phenyl-2-butenamide (m.p. 141°–142° C. as the oxalate salt); or
(w) 2-(1-aminoethylidene)-N-(2-dimethylaminoethyl)-4-methyl-N-phenyl-3-oxo-pentanamide (m.p. 95°–96° C. as the oxalate salt),
respectively.

EXAMPLE 3
2-Acetyl-3-Amino-N-(2-Dimethylaminoethyl)-N-(m-Fluorophenyl)-2-Pentenamide

Step 1.
N-(m-Fluorophenyl)-3-Ethyl-5-Methyl-4-Isoxazole Carboxamide

A mixture of 13.3 grams (0.120 mole) of m-fluoroaniline and 20.9 ml. (0.150 mole of triethylamine in 120 ml. of toluene is treated by dropwise addition with 22.5 grams (0.129 mole) of 3-ethyl-5-methyl-4-isoxazole carbonyl chloride in 100 ml. of toluene while maintaining the temperature between 30°–35° during addition. The mixture is stirred at room temperature overnight, filtered and the filtrate washed with 2N hydrochloric acid. The toluene is dried and evaporated with the residue recrystallized from toluene to give N-(m-fluorophenyl)-3-ethyl-5-methyl-4-isoxazole carboxamide (m.p. 99.5°–101° C.).

Step 2.
N-(m-Fluorophenyl)-N-(2-Dimethylaminoethyl)-3-Ethyl-5-Methyl-4-Isoxazole Carboxamide A mixture of 22.0 grams (0.0887 mole) of N-m-fluorophenyl-3-ethyl-5-methyl-4-isoxazole carboxamide and 4.4 grams (0.0921 mole) of 50% sodium hydride in oil in 500 ml. of dimethylformamide is stirred at room temperature for five hours. The resulting mixture is treated by dropwise addition with 9.68 grams (0.09 mole) of 2-dimethylaminoethyl chloride). The resulting mixture is heated at 60° C. for 20 hours. The mixture is cooled, poured onto ice water and extracted with ether. The ether is washed with 2N hydrochloric acid and the aqueous acidic layer made basic with sodium hydroxide and extracted with methylene chloride. The methylene chloride extract is dried with magnesium sulfate and evaporated to give N-(m-fluorophenyl)-N-(2-dimethylaminoethyl)-3-ethyl-5-methyl-4-isoxazole carboxamide as an oil.

Step 3.
2-Acetyl-3-Amino-N-(2-Dimethylaminoethyl)-N-m-Fluorophenyl-2-Pentenamide A mixture of 15.3 grams (0.048 mole) of N-(m-fluorophenyl)-N-(2-dimethylaminoethyl)-3-ethyl-5-methyl-4-isoxazole carboxamide and 1.5 grams of 10% palladium on carbon in 120 ml. of ethanol is hydrogenated at 50 psi at room temperature overnight. The catalyst is then removed by filtration and the solvent evaporated in vacuo. The residue is crystallized from ether; petroleum ether (1:1) to give 2-acetyl-3-amino-N-(2-dimethylaminoethyl)-N-(m-fluorophenyl)-2-pentenamide (m.p. 96°–97° C.).

What is claimed is:

1. A compound of the formula

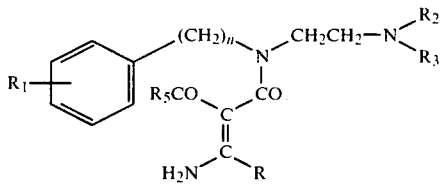

where
n is 0 or 1;
R is lower alkyl, or

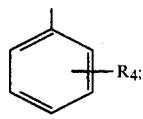

$R_2$ and $R_3$ are each, independently, lower alkyl,
$R_1$ and $R_4$ are each, independently, hydrogen, halo having an atomic weight of 19 to 36, lower alkyl or lower alkoxy, and
$R_5$ is hydrogen or alkyl of 1 to 6 carbon atoms,
or a pharmaceutically acceptable acid addition salt thereof.

2. A compound according to claim 1 in which n is 0.

3. A compound according to claim 2, in which $R_1$ is fluoro.

4. The compound of claim 1 which is 2-(aminophenylmethylene)-N-(2-dimethylaminoethyl)-N-phenyl-3-oxo-butanamide.

5. The compound of claim 1, which is 2-(aminophenylmethylene)-N-(2-dimethylaminoethyl)-N-benzyl-2-oxo-butanamide or 2-(aminophenylmethylene)-N-(2-diethylaminoethyl)-N-phenyl-3-oxo-butanamide.

6. The compound of claim 1, which is
(a) 2-(aminophenylmethylene)-N-(2-dimethylaminoethyl)-N-(p-fluorophenyl)-3-oxo-butanamide;
(b) 2-(aminophenylmethylene)-N-(2-dimethylaminoethyl)-N-(p-tolyl)-3-oxo-butanamide;
(c) 2-(aminophenylmethylene)-N-(2-dimethylaminoethyl)-N-(p-methoxyphenyl)-3-oxo-butanamide;
(h) 2-(aminophenylmethylene)-N-(2-diethylaminoethyl)-N-(m-fluorophenyl)-3-oxo-butanamide; and
(i) 2-(aminophenylmethylene)-N-(2-dimethylaminoethyl)-N-(m-fluorophenyl)-3-oxo-butanamide.

7. The compound of claim 1 which is 2-acetyl-3-amino-N-(2-dimethylaminoethyl)-N-phenyl-2-pentenamide.

8. The compound of claim 1, which is 2-acetyl-3-amino-N-(2-dimethylaminoethyl-N-(m-fluorophenyl)-2-pentenamide.

9. The compound of claim 1 which is 2-acetyl-3-amino N-(2-dimethylaminoethyl-N-(o-fluorophenyl)-2-pentenamide.

10. A compound of claim 1, which is selected from the group consisting of:
(k) 2-acetyl-3-amino-N-(2-dimethylaminoethyl)-N-benzyl-2-pentenamide;
(n) 2-acetyl-3-amino-N-(2-dimethylaminoethyl)-N-(p-fluorophenyl-2-pentenamide;
(o) 2-acetyl-3-amino-N-(2-diisopropylaminoethyl)-N-phenyl-2-pentenamide;
(p) 2-acetyl-3-amino-N-(2-dimethylaminoethyl)-N-(o-tolyl)-2-pentenamide;
(q) 2-acetyl-3-amino-N-(2-dimethylaminoethyl)-N-(o-methoxyphenyl)-2-pentenamide;
(r) 2-acetyl-3-amino-N-(2-diethylaminoethyl)-N-(o-fluorophenyl)-2-pentenamide;
(s) 2-formyl-3-amino-N-(2-dimethylaminoethyl)-N-phenyl-2-pentenamide;
(t) 2-propionyl-3-amino-N-(2-dimethylaminoethyl)-N-phenyl-2-pentenamide;
(u) 2-butyryl-3-amino-N-(2-dimethylaminoethyl)-N-phenyl-2-]pentenamide;
(v) 2-acetyl-3-amino-N-(2-dimethylaminoethyl)-N-phenyl-2-butenamide; or
(w) 2-(1-aminoethylidene)-N-(2-dimethylaminoethyl)-4-methyl-N-phenyl-3-oxo-pentanamide, respectively.

11. A pharmaceutical composition comprising a compound of claim 1 and a pharmaceutically acceptable diluent or carrier therefor.

12. A method for treating diabetes which comprises administering to an animal in need of said treatment a hypoglycemic effective amount of a compound of claim 1.

13. A method of treating diabetes by inhibiting postprandial hyperglycemia which comprises administering to an animal in need of said treatment an effective amount of a compound of claim 1.

* * * * *